United States Patent
Sheppard et al.

(10) Patent No.: US 6,500,153 B1
(45) Date of Patent: Dec. 31, 2002

(54) SYRINGE AND NEEDLE FOR PREVENTING INADVERTENT DRUG INJECTION

(75) Inventors: Ian Graham Sheppard, Burnaby (CA); Martin John Forbes, Richmond (CA); Theresia Trevan Fladl, Vancouver (CA); Ivan Yan-Yip Li, Vancouver (CA); John Hayward Emes, Richmond (CA); Jeffrey Howard Davis, Richmond (CA); Kathryn Ann Barbour, Vancouver (CA)

(73) Assignee: Children's and Women's Health Centre of British Columbia, Vancouver (CA)

( * ) Notice: Subject to any disclaimer, the term of this patent is extended or adjusted under 35 U.S.C. 154(b) by 0 days.

(21) Appl. No.: 09/903,857

(22) Filed: Jul. 13, 2001

(51) Int. Cl.$^7$ .............................................. A61M 5/178
(52) U.S. Cl. ........................... 604/164.07; 604/164.01; 604/187; 604/188; 604/240; 604/241; 604/243
(58) Field of Search ................. 604/164.01, 164.07, 604/187, 188, 240, 241, 243, 285; 285/332, 332.1, 354, 384–388, 247, 283

(56) References Cited

U.S. PATENT DOCUMENTS

| | | | |
|---|---|---|---|
| 4,511,356 A | | 4/1985 | Froning et al. ............. 604/164 |
| 5,098,406 A | | 3/1992 | Sawyer ........................ 604/247 |
| 5,267,983 A | * | 12/1993 | Oilschlager et al. ........ 604/283 |
| 5,312,375 A | * | 5/1994 | Gurmarnik .................. 604/264 |
| 5,616,133 A | | 4/1997 | Cardenas .................... 604/187 |
| 5,620,427 A | | 4/1997 | Werschmidt et al. ....... 604/283 |
| 5,651,775 A | * | 7/1997 | Walker et al. .............. 604/207 |
| 5,656,035 A | | 8/1997 | Avoy ........................... 604/191 |
| 5,846,226 A | | 12/1998 | Urmey ......................... 604/158 |
| 5,941,853 A | | 8/1999 | Collins ........................ 604/165 |
| 6,112,743 A | * | 9/2000 | Denton .................. 128/200.14 |
| 6,273,478 B1 | * | 8/2001 | Benett et al. ............... 285/346 |
| 6,402,207 B1 | * | 6/2002 | Segal et al. ................. 285/330 |

OTHER PUBLICATIONS

American National Standard for Medical Materiel Luer Taper Fittings Performance (1984).
International Standard ISO 594/1 Conical Fittings with 6% (Luer) taper for syringes, needles and certain other medical equipment—Part 1: Gerneral Requirements (Jun. 15, 1986).
International Standard ISO 594–2 Conical fittings with a 6% (Luer) taper for syringes, needles and certain other medical equipment—Part 2: Lock Fittings (Sep. 1, 1998).
CEN Report Luer Connectors—A report to CEN chef from the CEN forum task group "Luer fittings" (Feb. 2000).
Federal Standard Syringe, Luer, Interchangeable Component, Dimensions of (Feb. 6, 1961).

* cited by examiner

*Primary Examiner*—David J. Walczak
*Assistant Examiner*—Anuradha Ramana
(74) *Attorney, Agent, or Firm*—Bull, Housser & Tupper (57) ABSTRACT

A spinal syringe and needle for preventing the inadvertent injection of an intravenous drug spinally includes a needle engagement extension on the spinal needle defining an opening of a first diameter, a syringe engagement extension on the spinal syringe defining an opening of a second diameter, the syringe engagement extension engageable with the needle engagement extension to operatively connect the needle to the syringe. The first and second diameters are dimensioned such that a surface of the syringe engagement extension is in frictional engagement with a surface of the needle engagement extension, the first diameter is substantially the same as the diameter of an opening defined by the engagement extension of a typical syringe and the second diameter is substantially the same as the diameter of an opening defined by the engagement extension of a typical needle. A system and method for preventing the inadvertent injection of an intravenous drug spinally and a spinal drug intravenously includes a spinal needle and a spinal syringe for holding and dispensing the drug to be injected spinally, the spinal syringe operatively connectable to the spinal needle. An intravenous syringe is provided for holding and dispensing the drug to be injected intravenously, the intravenous syringe operatively connectable to the intravenous needle. The intravenous needle cannot be operatively connected to the spinal syringe and the spinal needle cannot be operatively connected with the intravenous syringe thereby preventing the inadvertent injection of the drug in each syringe through an incorrect needle.

35 Claims, 5 Drawing Sheets

SYRINGE AND NEEDLE FOR PREVENTING INADVERTENT DRUG INJECTION

FIELD OF THE INVENTION

The present invention generally relates to a syringe and needle, and a system which incorporates that syringe and needle in combination, for preventing inadvertent injection of a drug and more specifically relates to a syringe for spinal drug injection which is incompatible with a typical needle and a needle for spinal drug injection which is incompatible with a typical syringe.

BACKGROUND OF THE INVENTION

Drugs may be injected into patients using a needle (or "cannula") by several different methods, including injection into a vein ("intravenously") or injection into the fluid around the spine ("spinally"), including intrathecally, epidurally and intramedurally. Drug treatment for particular ailments may at times require the injection of a drug in a very specific manner. For example, it is often of critical importance to ensure that drugs intended for intravenous injection are not mistakenly injected spinally and vice versa. It is also important to ensure that a drug contained in a syringe for injection in a particular manner is not mistakenly attached to a needle used for inappropriate injection of that drug thereby increasing the risk that the drug will be mistakenly injected in an inappropriate manner. For example, to ensure that a drug intended for intravenous injection stored in a syringe is not mistakenly attached to a spinal needle and injected spinally.

This is of particular concern in the field of chemotherapy where very toxic drugs employed to treat particular types of cancer must be injected in a very specific manner. For example a group of drugs known as "vinca alkaloids" are extremely toxic when administered in any manner other than intravenously. If these drugs are administered in any other manner, including spinally, these drugs may be fatal to the patient.

There have been unfortunate occurrences of mistaken injection of a vinca alkaloid drug used in chemotherapy into a patient's spinal region, rather than by the appropriate method of injection, that being intravenously. A syringe containing such a drug can be accidentally attached to a spinal needle and the drug injected spinally into the patient, thereby causing death or serious injury to the patient.

As well, a drug in a syringe which is intended to be injected spinally may be attached to a needle used for intravenous injection and the drug mistakenly injected intravenously.

Many of these inadvertent injections can be attributed to human error in either filling a given syringe intended for spinal injection of drugs with a toxic drug intended for intravenous injection or mixing up syringes containing various chemotherapy drugs and attaching a syringe containing a toxic drug intended for intravenous injection to a spinal needle and injecting that drug spinally into the patient.

As a result there is a significant need for the development of a syringe and needle which may be employed for spinal injection of a drug intended for spinal injection and a system incorporating a combination of that syringe and needle which will reduce the risks inherent in handling and injecting toxic drugs meant to be injected only in a very specific manner. The present invention is intended to accomplish this by reducing the opportunity for human error in handling and injecting toxic drugs in the appropriate manner into patients receiving those drugs.

SUMMARY OF THE INVENTION

In one embodiment of the invention a spinal syringe is operatively connectible with a spinal needle for spinal injection of a drug. The syringe is incompatible for operative connection with a connector of a typical needle. The spinal syringe includes a nozzle for operatively connecting the syringe to the spinal needle, the nozzle having a conduit extending axially therethrough for delivery of the drug from the syringe to the needle and includes an outer tip. The tip extends about an outer end of the conduit and is dimensioned to contact the outer end of the connector of the typical needle to prevent operative connection of the spinal syringe with the typical needle.

In another embodiment of the invention, a spinal needle is operatively connectible with a spinal syringe for spinal injection of a drug. The spinal syringe includes a nozzle with a conduit extending axially therethrough. The needle is incompatible for operative connection with the nozzle of a typical syringe, the nozzle having an outer tip. The needle includes a connector cooperating with the nozzle of the spinal syringe to operatively connect the spinal syringe to the spinal needle to dispense the drug. The connector includes an outer end dimensioned to contact the outer tip of the nozzle of the typical syringe to prevent operative connection of the spinal needle with the typical syringe.

In yet another embodiment of the invention, a spinal syringe and a spinal needle combination are operatively connectible with one another for spinal injection of a drug. The spinal syringe is incompatible for operative connection with a connector of a typical needle, the connector of the typical needle having an outer end. The spinal needle is incompatible for operative connection with the nozzle of a typical syringe, the nozzle having an outer tip. The spinal syringe including a nozzle for operatively connecting the spinal syringe to the spinal needle, the nozzle having a conduit extending axially therethrough for delivery of the drug from the spinal syringe to the spinal needle and including an outer tip. The tip extending about an outer end of the conduit dimensioned to contact the outer end of the connector of the typical needle to prevent operative connection of the spinal syringe with the typical needle. The spinal needle includes a connect or cooperating with the nozzle of the spinal syringe to operatively connect the spinal syringe to the spinal needle to dispense the drug. The connector includes an outer end dimensioned to contact the outer tip of the nozzle of the typical syringe to prevent operative connection of the spinal needle with the typical syringe.

In another embodiment a spinal syringe and needle for preventing the inadvertent injection of an intravenous drug spinally includes, in combination, a needle engagement extension on the spinal needle defining an opening of a first diameter, a syringe engagement extension on the spinal syringe having a nozzle of a second diameter, the syringe engagement extension engageable with the needle engagement extension to operatively connect the needle to the syringe. The first and second diameters are dimensioned such that a surface of the syringe engagement extension is in frictional engagement with a surface of the needle engagement extension, the first diameter is smaller than the diameter of the nozzle of a typical syringe and the second diameter is larger than the diameter of the opening of a typical needle.

In a further embodiment, a system and method for preventing the inadvertent injection of a spinal drug intravenously and an intravenous drug spinally includes, in combination, a spinal needle and a spinal syringe for holding and dispensing the drug to be injected spinally, the spinal drug operatively connectable to the spinal needle. An intravenous and intravenous syringe are provided for holding and dispensing the drug to be injected intravenously, the intravenous syringe operatively connectable to the intravenous needle. The intravenous needle cannot be operatively connected to the spinal syringe thereby preventing the inadvertent injection of the drug in the spinal syringe through the intravenous needle and the spinal needle cannot be operatively connected with the intravenous syringe thereby preventing the inadvertent injection of the drug in the intravenous syringe through the spinal needle.

In another embodiment, the spinal needle may include a first Luer lock portion at an end of the spinal needle and the spinal syringe can comprise a second Luer lock portion at its end which mates with the first Luer lock portion to operatively connect the spinal needle with the spinal syringe. In yet another embodiment, the intravenous needle may include a first slip fit portion on an end and the intravenous syringe may include a second slip fit portion which mates with the first slip fit portion of the intravenous needle to operatively connect the intravenous needle with the intravenous syringe.

DETAILED DESCRIPTION

Figure 1:
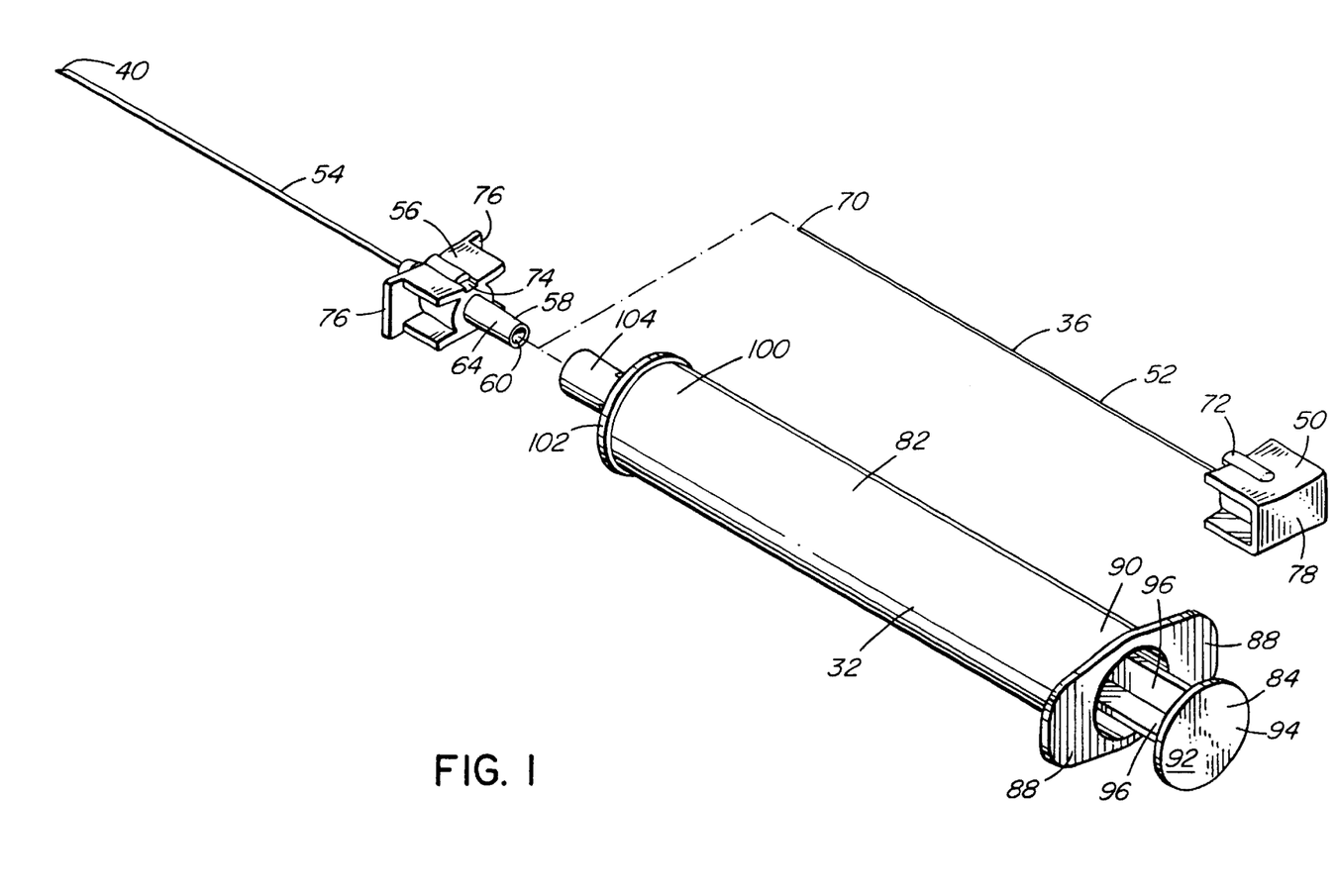
FIG. 1 is a perspective view of a spinal needle, syringe and stylette.

FIG. 1 depicts the uniquely dimensioned spinal syringe 32 and needle 34 of the present invention which are incompatible for use with a typical syringe and needle. As used herein, the term "typical syringe" and "typical needle" means a syringe and needle typically used by the medical profession meeting the ANSI/HIMA "American National Standard for Medical Material-Luer Taper Fittings-Performance MD70.1-1983 (Revision of ANSI Z70.1-1955). The standard provides the following dimensions, including tolerances, for the following elements of "typical" syringes and needles:

| COMPONENT | SIZE (IN MILLIMETRES) |
|---|---|
| Inside diameter of the needle socket opening, at large end (Reference 120 of FIG. 6) | Minimum 4.270 Maximum 4.315 |
| Lug-to-lug diameter (Reference 158 of FIG. 6) | Minimum 7.73 Maximum 7.83 |
| Outside diameter of end of syringe nozzle (Reference 115 of FIGS. 4 and 5) | Minimum 3.925 Maximum 3.990 |

Figure 3:
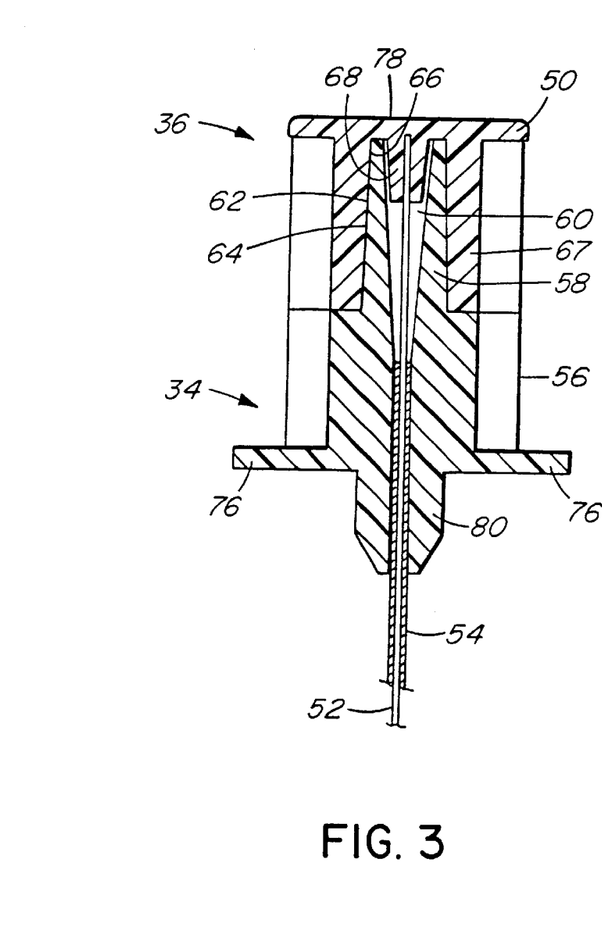
FIG. 3 is a fragmentary sectional view of the spinal needle and its corresponding stylette.

Syringe 32 may be operatively connected to needle 34 for injection of the drug in syringe 32 through needle 34 into a patient. Needle 34 includes cannula 54 which extends from one end of head 56. Stylette 36 may be inserted axially through cannula 54 needle 34 (as best seen in FIG. 3) and includes generally rectangular-shaped head 50 attached at one end of elongated stylette portion 52. Stylette portion 52 is dimensioned to fit within hollow inner opening of needle 34.

Referring to FIGS. 1 and 3 head 56 includes extension 58 extending axially from the end of head 56 opposite to cannula 54. Extension 58 includes opening 60 therein extending axially through head 56 and connecting to opening in cannula 54. Head 50 of stylette 36 includes opening 62 defined by inner surface 66 of flange 67 extending axially within head 50 and dimensioned to contact outer surface 64 of extension 58 such that, when engaged with one another as depicted in FIG. 3, outer surface 64 of extension 58 lies adjacent inner surface 66 of opening 62.

Figure 7:
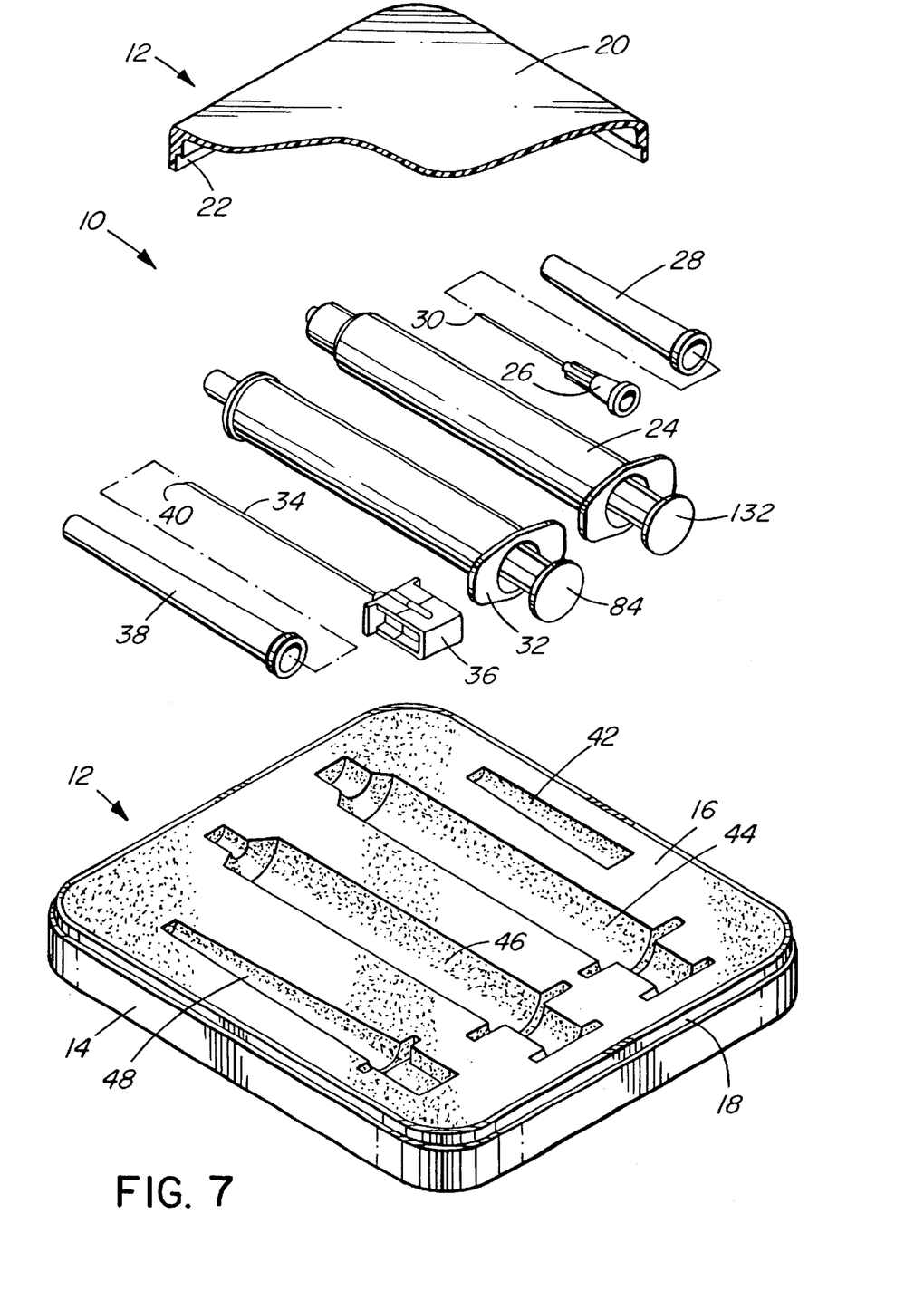
FIG. 7 is a perspective illustration of a system for preventing the inadvertent injection of a spinal drug intravenous and an intravenous drug spinally.

As best seen in FIG. 3 stylette portion 52 is attached axially to head 50 through axial extension 68. Stylette portion 52 is thereby retained rigidly within head 50 and extends axially from extension 68 through openings 60 and 62 and then through cannula 54 of needle 34. The distal end of stylette opposite to the end attached to extension 68 is angled to present a sharp tip 70 at its outer end and stylette portion 52 is dimensioned in length so as to be generally co-terminus with tip 40 when stylette 36 is inserted into needle 34 as depicted in FIG. 3 and FIG. 7.

Referring to FIG. 1, head 50 includes flange 72 extending in the direction of tip 70. Head 56 includes a corresponding slot 74 which accepts tip 72 therein when stylette 36 is positioned within needle 34. Cannula 54 includes tip 40 which is likewise angled to present a sharp point for ease of insertion of cannula 54 into the patient. When flange 72 is positioned within slot 74 the angled portions of tips 40 and 70 are maintained in alignment which facilitates insertion of cannula 54 with stylette portion 52 into the patient.

Head 56 also includes a pair of opposed wing members 76 extending laterally from the longitudinal axis of needle 34. Head 50 includes platform 78 at the proximal end of head 50 opposite to the end from which stylette portion 52 extends. Platform 78 and wing member 76 are used to facilitate insertion of needle 54 with stylette 36 into the patient as part of the appropriate procedure for inserting needle 34 into the patient for spinal injection of a drug. Wings 76 are used for gripping the index and middle fingers of the person inserting the needle and platform 78 is used as a contact point for the thumb to assist in the insertion of needle 34 and stylette 36 into the patient.

Head 56 also includes cannula support extension 80 which serves to support cannula 54 within head 56 thereby reducing the opportunity for lateral movement or bending of cannula 54 when pressure is applied on tip 40 as cannula 54 is inserted into the patient.

Figure 2:
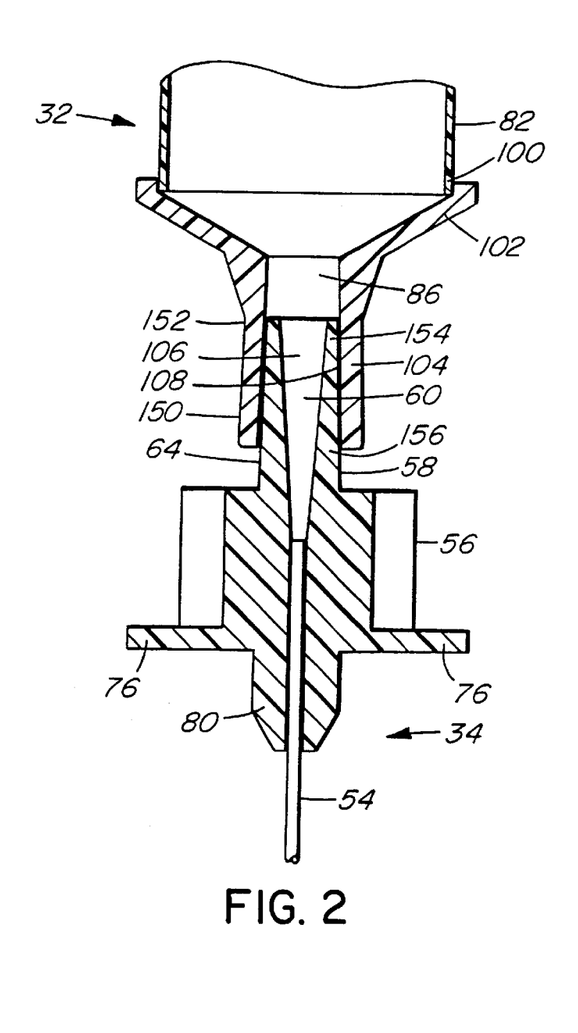
FIG. 2 is a fragmentary enlarged sectional view of the slip fit attachment end of a spinal syringe attached to the slip fit attachment end of a spinal needle.

Referring to FIG. 1 and FIG. 2, needle 54 may be attached to syringe 32 in order to dispense the drug in syringe 32 through needle 34 into the patient. Syringe 32 includes storage region 82 for storing the drug to be injected spinally into the patient. Plunger 84 extends into first end 90 of region 82. Plunger 84 is used in a typical manner and when depressed within region 82 puts pressure on the drug in region 82 to cause the drug to flow through needle 34 into the spinal region of the patient. Syringe 32 also includes end opening 86 extending axially from one end of storage region 82 to permit the drug within storage region 82 to exit syringe 32 through opening 86 into opening 60 of extension 58 when plunger 84 is depressed.

Syringe 32 further includes a pair of opposed wing members 88 extending from a first end 90 of region 82. Plunger 84 includes platform 92 on plate 94 which extends in a plane perpendicular to the longitudinal axis of plunger 84. Plunger 84 further includes longitudinal axial extension ribs 96 extending from plate 94 at one end to inner sealed resilient member (not shown) which provides a seal between plunger 84 and inner wall (not shown) of storage region 82 to prevent leakage of drugs past inner sealed resilient member on depression of plunger 84 into storage region 82.

Second end 100 of storage region 82 includes securing member 102 rigidly secured to end 100 about the periphery of end 100. Securing member 102 further includes axial extension 104 forming opening 106 therein. Inner wall 108 of extension 104 is dimensioned similar to inner surface 66 of head 50 and accepts extension 58 therein such that outer surface 64 contacts inner wall 108. However in this case inner wall 108 is dimensioned to more tightly engage outer surface 64 to provide a relatively secure friction fit engagement between inner wall 108 and outer surface 64. This ensures that there is sufficient frictional force between inner wall 108 and outer surface 64 to prevent separation of syringe 32 from needle 34 when syringe 32 is moved outwardly from the patient to remove needle 34 from that patient after the drug in storage region 82 has been injected spinally into the patient. To assist in securing these components surfaces 64 and 108 may be conically-shaped with a larger diameter at the outer end 150 of extension 104 as compared to inner end 152. Correspondingly, the outer end 154 of extension 58 is of a small diameter as compared to inner end 156 of extension 58. This facilitates the alignment and insertion of extension 54 into extension 104 to frictionally engage with one another. The taper of surfaces 64 and 108 is the same, preferably about 6 percent (that is a change of 0.060 millimeters in diameter per 1 millimeter length).

Figure 4:
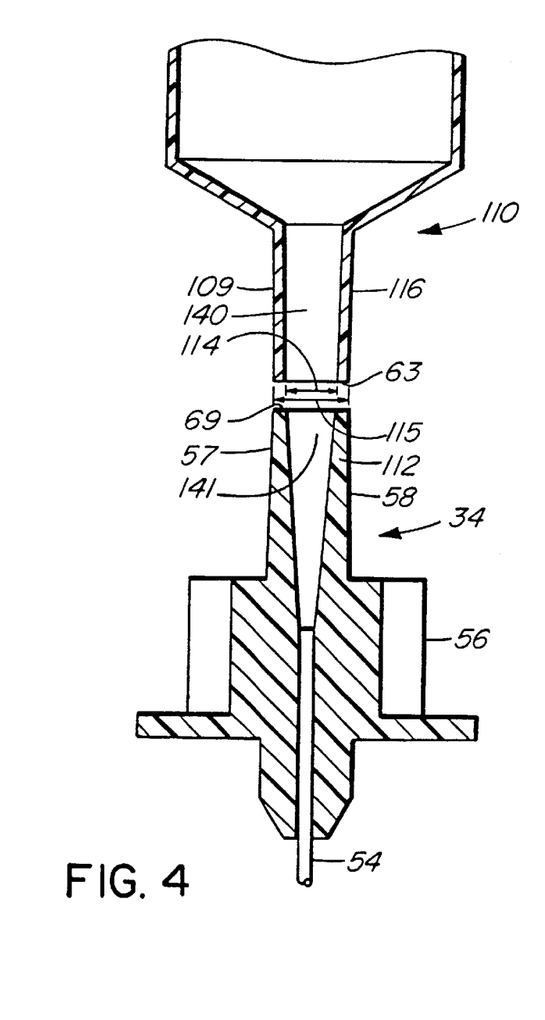
FIG. 4 is a fragmentary sectional view of an attachment end of a typical syringe commonly used by the medical profession adjacent to, but not attached to, the uniquely dimensioned attachment end of the spinal needle of the present invention.

As discussed below with respect to FIG. 7, syringe 24 is of standard size containing a tip suitable for attaching slip fit Luer lock combination needle 26. FIG. 4 depicts slip fit syringe 110 typically employed by the medical profession and of standard dimension as described above. Syringe 110 is shown adjacent spinal needle 34 of the present invention. Wall 112 of extension 58 of needle 34 is circular of inner diameter 114 at end 69 forming opening 141. Wall 116, which is also circular, of nozzle 109 is also of inner diameter 114 at tip 63 forming opening 140. Wall 116 cannot extend about wall 112 in order to engage and secure needle 34 to syringe 110 in an operative manner. Wall 116 cannot fit within wall 112 into opening 141 as the diameter of wall 112 and 116 are the same. If tip 63 of syringe 110 is moved to a position against extension 58, end 69 of connector 57 contacts tip 63 of syringe 110. As a result it is not possible to operatively attach syringe 110 to needle 34.

Figure 5:
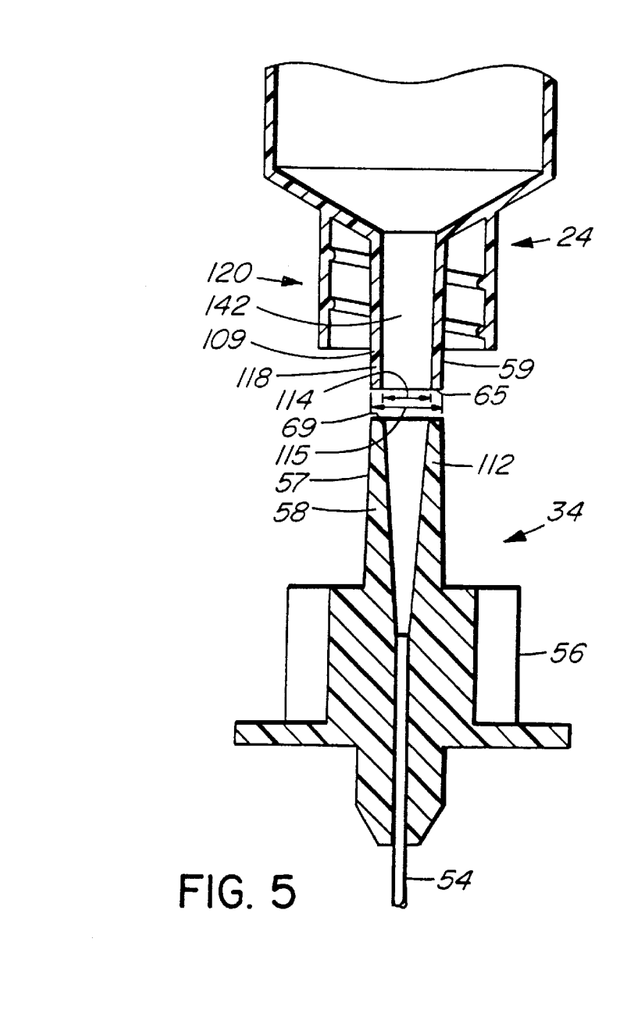
FIG. 5 is a fragmentary sectional view of a the attachment end of a typical syringe commonly used by the medical profession adjacent to, but not attached to, the uniquely dimensioned attachment end of the spinal needle of the present invention.

FIG. 5 depicts a typical Luer lock syringe 24 adjacent spinal needle 34 of the present invention. Luer lock syringe 24 is of a standard diameter typically used by the medical profession for drug injection. Syringe 24 includes extension or nozzle 59 having a circular wall 118 forming an opening 142 of diameter 114, that is equivalent to diameter 114 of syringe 110 depicted in FIG. 4. A typical Luer lock syringe 24 includes end 120 which accepts either a typical Luer lock needle or a typical slip fit needle therein for attachment of the syringe to a typical Luer lock or slip fit needle. However in the case of spinal needle 34 wall 112 is circular of diameter 114, the same diameter as wall 118. Outer end 59 of connector 57 of wall 112 will contact outer tip 65 of wall 118 thereby preventing operative connection of syringe 24 to needle 34.

As discussed above, a typical syringe 110, 120 has an outside diameter 115 between 3.925 millimeters and 3.990 millimeters at tip 63, 65 of nozzle 109. Therefore, in order to ensure that needle 34 of the present invention may not be operatively connected to nozzle 109 of a typical slip fit syringe 110 (FIG. 4) or a lure lock syringe 120 (FIG. 5) inner diameter 114 of wall 112 at end 69 must be less than the outer diameter 115 of wall 116 at tip 63. This means that the inner diameter 114 of wall 112 must be less than the minimum possible outside diameter 115 of wall 116, or less than 3.925 millimeters.

As well, outer diameter 115 of wall 112 must be greater than the inner diameter 114 of wall 116. Otherwise extension 58 could be inserted into opening 140 of syringe 110 or opening 142 of syringe 120 (FIGS. 4 and 5 respectively). The inner diameter 114 of wall 116 is not specified in the ANSI/HIMA standard for a typical syringe as provided above. The minimum outer diameter of wall 112 at end 69 must therefore be estimated based on a reasonable thickness of wall 116 in order to approximate the largest possible inner diameter 114 of wall 116. Based on a minimum realistic wall thickness of 0.25 millimeters inner diameter 114 of wall 116 can be no more than 3.49 millimeters for a semi-rigid syringe (that is 3.925 minus 0.5 millimeters) or 3.527 millimeters for a rigid syringe (4.027 minus 0.5 millimeters). In order to ensure incompatibility, the outside diameter 115 of wall 112 must be greater than 3.49 millimeters for a semi-rigid syringe and greater than 3.527 millimeters for a rigid syringe. In order to ensure incompatibility with both semi-rigid and rigid syringes, the outside diameter must be greater than 3.527 millimeters.

Figure 6:
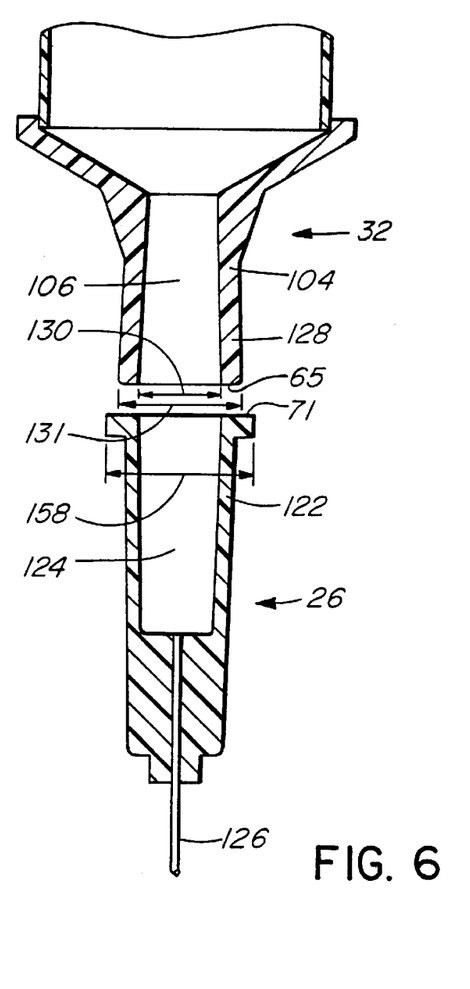
FIG. 6 is a fragmentary sectional view of the uniquely dimensioned attachment end of a syringe of the present invention adjacent to, but not attached to, a standard attachment end of a slip fit needle commonly used by the medical profession.

FIG. 6 depicts a typical needle 26 adjacent spinal syringe 32 of the present invention. Needle 26 is a typical slip fit/Luer lock combination needle used in the medical profession for injection of drugs. Needle 26 includes circular wall 122 forming opening 124 to receive a drug from a standard slip fit or Luer lock syringe such as syringe 24 and pass the drug through cannula 126 for injection into a patient. Wall 122 is of inner diameter 130. Syringe 32 includes extension 104 with circular wall 128 forming opening 106. Wall 128 is also of inner diameter 130 at outer tip 65, the same as the inner diameter of wall 122. Syringe 32 may not be operatively connected to needle 28 as wall 128 and wall 122, being of the same inner diameter, contact each other preventing operative connection of those components. That is, outer tip 65 of wall 128 will contact outer end 71 of wall 122 preventing extension 104 from entering opening 124.

A typical needle has an outside lug to lug diameter of between 7.73 millimeters and 7.83 millimeters. In order to ensure that syringe 32 of the present invention may not be operatively connected to a typical needle 26 inner diameter 130 of wall 128 must be less than the minimum outer diameter, lug to lug, of wall 122 at tip 71. This means that inner diameter 130 of wall 128 at tip 65 must be less than 7.73 millimeters.

As well, outer diameter 131 of wall 128 at tip 65 must be greater than the maximum inner diameter 130 of wall 122 at tip 71. As the maximum inner diameter 130 of wall 122 is 4.315 millimeters in accordance with the ANSI/HIMA standard, outer diameter 131 of wall 128 at tip 65 must be greater than 4.315 millimeters.

Referring to FIG. 4, a typical slip-fit syringe 110 has nozzle 109 with circular wall 116 outer diameter 115 at tip 63 of between about 3.925 millimeters and 3.990 millimeters. Similarly, with reference to FIG. 5, a typical Luer lock syringe 24 has an extension 59 with circular wall 118 outer diameter 115 at tip 65 of between about 3.925 millimeters and 3.990 millimeters. In order to prevent operative connection of a needle 34 to syringe 24 or syringe 110, extension 58 of needle 34 wall 112 outer diameter 115 at outer end 69 must be greater than inner diameter 114 of syringes 24 and 110. As well, inner diameter 114 of wall 112 at outer end 69 of syringe 34 must be less than 3.925 millimeters to prevent the smallest possible outer diameter nozzle 109 or extension 59 from being inserted into opening 60.

Referring to FIG. 6, and based on the above ANSI standards, a typical Luer lock and slip fit needle 26 has wall 122 of inner diameter 130 at outer end 65 of about between 4.270 millimeters and 4.315 millimeters. Consequently in order to prevent operative connection of needle 26 with syringe 32 of the present invention extension 104 with wall 128 is of outer diameter 131 greater than 4.315 millimeters in order to prevent extension 104 from entering opening 124. As well the typical needle has a lug-to-lug outer diameter between about 7.73 millimeters and 7.83 millimeters.

Extension 104 inner diameter 130 must be less than 7.73 millimeters (the smallest possible outer lug-to-lug diameter of wall 122) in order to prevent extension 104 from extending over wall 122 to engage needle 26. This ensures that neither spinal needle 34 nor spinal syringe 32 may be operatively connected to a typical Luer lock and slip fit syringe 24 (FIG. 5) or a typical slip fit syringe 110 (FIG. 4) found in hospitals and other places where drugs are administered thereby preventing drugs in those syringes from being injected spinally using spinal needle 34. As well, a typical needle 26 (FIG. 6) found in hospitals and in other places where drugs are injected typically used for intravenous injection cannot be operatively connected to syringe 32 of the present invention thereby preventing inadvertent injection of the spinal drug in spinal syringe 32 through intravenous needle 26 intravenously into a patient.

FIG. 7 depicts a system for preventing the inadvertent injection of a spinal drug intravenously and an intravenous drug spinally generally at 10. System 10 comprises a kit combining the various components necessary for preventing inadvertent injection which components are all located in container 12. Container 12 comprises hard shell bottom member 14 with soft housing member 16 extending within a cavity formed in bottom member 14. Bottom member 14 includes indent 18 about the upper and outer circumference of bottom member 14. Cover 20 is dimensioned to extend over the upper part of bottom member 14 to cover housing member 16. Cover 20 includes lip 22 which mates with indent 18 to secure cover 20 to bottom member 14. Cover 20 may be made of clear plastic material so that the components housed in container 12 may be viewed from outside container 12.

System 10 further includes a standard Luer lock and slip fit combination syringe 24 with a corresponding slip fit and Luer lock needle 26 which is attachable to syringe 24. Cover 28 extends over needle 26 to protect needle 26 and prevent inadvertent contact with tip 30 of needle 26. Container 12 also includes uniquely dimensioned slip fit syringe 32 used for spinal injection of a drug. Spinal needle 34 which mates with syringe 32 is also included in container 12 with a corresponding stylette 36 extending longitudinally through needle 34. Cover 38 extends over needle 34 to protect needle 34 and prevent inadvertent contact with tip 40 of needle 34. Both needle 34 and needle 26 have hollow openings extending longitudinally therethrough to permit flow if drugs into a patient. The hollow opening of needle 34 is dimensioned to receive stylette 36 therein.

Syringe 24 and needle 26 are of size and shape typically used in hospitals and by the medical profession for intravenous injection of drugs or for other suitable drug injection methods as required for patient care. Spinal syringe 32 and needle 34 have uniquely dimensioned engaging extensions and are used solely for spinal injection of a drug.

Housing member 16 includes a plurality of indented regions to hold the various components previously described. Indented portion 42 is particularly dimensioned such that cover 28 containing needle 26 may be held in place portion 42.

Similarly indent 44 is dimensioned to hold syringe 24 therein. Indented portion 46 is dimensioned to hold spinal syringe 32 therein and indented portion 48 is dimensioned to hold stylette 36 (extending through needle 34), needle 34 and cover 38 therein.

All the components of system 10 forming the kit may be conveniently housed within container 12 to be used together for simultaneous treatment and injection of drugs both spinally using syringe 32, stylette 36 and needle 34 and intravenously using syringe 24 and needle 26.

Operation

Spinal syringe 32 (FIGS. 1, 2 and 6) is intended solely for use in injecting spinal drugs, and is carefully filled only with a spinal drug. Indicia (not shown) may be marked on the body of spinal syringe 32 warning individuals filling that syringe that only a drug intended for spinal injection is to be placed in the storage region 83 of syringe 32. Syringe 32, filled with a drug intended for spinal injection, may then be delivered to the patient at the place of injection. The doctor, or other health care provider cannot attach a typical needle 26 to syringe 32 due to the incompatible dimensioned as described earlier, thereby preventing injection of a drug in storage region 82 through a typical needle 26.

Spinal needle 34, which is compatible for operative use with syringe 32 is prepared for insertion into the patient's spinal region by first inserting stylette 36 into needle 34 as depicted in FIGS. 1 and 3. Wing members 76 are used to accommodate the index and first finger of the medical practitioner and the thumb is placed on platform 78 in order to guide cannula 54 with stylette 36 inserted therein so that tip 40 and 70 enter the patient's spinal region where the drug is to be injected.

Stylette 36 is then removed from needle 34, leaving needle 34 in position in the patient. Syringe 32 is then attached to needle 34 by friction-fit engagement between outer surface 64 of extension 58 of needle 34 and inner wall 108 of extension 104 of syringe 32, as depicted in FIG. 2. Opening 86, connected to storage area 82 is thereby aligned with and connected to opening 106 of needle 34. Opening 106 is connected to cannula 54 with tip 40 extending into the spinal region of the patient.

Plunger 84 is depressed into storage region 82 to force the drug in storage region 82 through opening 86, opening 106 and cannula 54 into the patient's spinal region. This properly directs the drug in storage region 82 into the spinal region of the patient.

A drug intended for injection in areas other than the patient's spinal region, for example those intended strictly for intravenous injection, cannot inadvertently be connected to needle 34, whether positioned within the patient for spinal injection with tip 40 in the spinal region of the patient, or otherwise. This prevents the inadvertent injection of a drug in a typical syringe 24 into the spinal region of a patient through spinal needle 34.

Referring to FIG. 7, system 10 would generally be provided to a medical practitioner in situations where a spinal drug is to be administered to a patient either concurrently with the administration of another drug intravenously or in a situation where there may be a danger of misinjection by confusing drugs in particular syringes with needles used to inject drugs into specific regions of a patient's body. If all needles present can be attached to syringes containing these drugs human error can occur causing drugs to be injected in an inappropriate manner through the mistaken attachment of a syringe containing a drug meant to be injected in one manner, such as intravenously, to a needle used for injection in another manner, such as spinally.

The present invention overcomes this problem by providing a uniquely dimensioned spinal syringe 32, together with a uniquely dimensioned spinal needle 34 which is operatively attachable to syringe 32. As well system 10 includes a typical Luer lock/slip fit combination syringe 24 and a typical slip fit and Luer lock needle 26 which may be operatively connected to syringe 24. However, as previously discussed, syringe 24 may not be operatively connected to needle 34 and syringe 32 may not be operatively connected to needle 26.

In a situation where a patient is to be injected with two different drugs, one spinally and the other intravenously, the spinal drug is placed in syringe 32 and the intravenous drug is placed in syringe 24.

For intravenous injection of the intravenous drug syringe 24 is operatively connected to needle 26 which is inserted into the patient's vein and the drug injected into that vein in typical fashion by depressing plunger 84.

Spinal injection of the drug in syringe 32 is undertaken by inserting stylette 36 into needle 34 as depicted in FIGS. 3 and 7 and pushing spinal needle into the patent's back region until tip 40 enters the spinal region of that patient. Stylette 36 is then removed and spinal syringe 32 then attached to needle 34 while it is still in this region of the patient. Plunger 84 is then depressed in the usual manner in order to inject the spinal drug through needle 34 and out tip 40 into the spinal region of that patient. It can be seen that the drug in syringe 24 cannot be mistakenly injected spinal into the patient through needle 34 due to the fact that the diameter of wall 118 of syringe 24 is substantially equal to the diameter of wall 112 of needle 34 preventing operative connection of those two components, as depicted in FIG. 5.

Similarly, it is impossible for the drug in syringe 32 to be injected intravenously through needle 26 as these two components cannot be operatively connected due to the fact that wall 122 and needle 26 and wall 128 of syringe 32 are the same diameter 130, as depicted in FIG. 6.

While the present invention has been illustrated by the description of an embodiment thereof, and while the embodiment has been described in considerable detail, it is not intended to restrict or in any way limit the scope of the appended claims to such detail. The invention in its broader aspects is therefore not limited to the specific details, representative apparatus and method and illustrative examples shown and described. Accordingly, departures may be made from such details without departing from the scope or spirit of Applicant's general inventive concept.

What is claimed is:

1. A spinal syringe operatively connectable with a spinal needle for spinal injection of a drug, the syringe being incompatible for operative connection with a connector of a typical needle the connector having an outer end, the syringe comprising:
   (a) a nozzle for operatively connecting the syringe to the spinal needle, the nozzle having a conduit extending axially therethrough for delivery of the drug from the syringe to the needle and comprising an outer tip;
   (b) the tip extending about an outer end of the conduit dimensioned to contact the outer end of the connector of the typical needle to prevent operative connection of the syringe with the typical needle.

2. The syringe of claim 1 wherein the tip is circular with an outer diameter greater than 4.315 and an inner diameter less than 7.73 millimeters.

3. The syringe of claim 2 wherein the inner diameter is less than the outer diameter by at least 0.5 millimeters.

4. A spinal needle operatively connectable with a spinal syringe for spinal injection of a drug, the spinal syringe having a nozzle with a conduit extending axially therethrough, the needle being incompatible for operative connection with a nozzle of a typical syringe the nozzle having an outer tip, the needle comprising:
   (a) a connector cooperating with the nozzle of the spinal syringe to operatively connect the spinal syringe to the spinal needle to dispense the drug;
   (b) the connector comprising an outer end dimensioned to contact the outer tip of the nozzle of the typical syringe to prevent operative connection of the spinal needle with the typical syringe.

5. The needle of claim 4 wherein the outer end is circular with an outer diameter greater than 3.527 millimeters and an inner diameter less than 3.925 millimeters.

6. the syringe of claim 5 wherein and the inner diameter is less than the outer diameter by at least 0.5 millimeters.

7. A spinal syringe and spinal needle combination operatively connectable with one another for spinal injection of a drug, the spinal syringe being incompatible for operative connection with a connector of a typical needle the connector of the typical needle having an outer end, and the spinal needle being incompatible for operative connection with a nozzle of a typical syringe, the nozzle of the typical syringe having an outer tip,
   (A) the spinal syringe comprising:
      (a) a nozzle for operatively connecting the spinal syringe to the spinal needle, the nozzle having a conduit extending axially therethrough for delivery of the drug from the spinal syringe to the spinal needle and comprising an outer tip;
      (b) the tip extending about an outer end of the conduit dimensioned to contact the outer end of the connector of the typical needle to prevent operative connection of the spinal syringe with the typical needle.
   (B) the spinal needle comprising:
      (a) a connector cooperating with the nozzle of the spinal syringe to operatively connect the spinal syringe to the spinal needle to dispense the drug;
      (b) the connector comprising an outer end dimensioned to contact the outer tip of the nozzle of the typical syringe to prevent operative connection of the spinal needle with the typical syringe.

8. The combination of claim 7 wherein the tip is circular with an outer diameter greater than 4.315 and an inner diameter less than 7.73 millimeters.

9. The combination of claim 8 wherein the inner diameter is less than the outer diameter by at least 0.5 millimeters.

10. The combination of claim 7 wherein the outer end is circular with an outer diameter greater than 3.527 millimeters and an inner diameter less than 3.925 millimeters.

11. The combination of claim 10 wherein the inner diameter is less than the outer diameter by at least 0.5 millimeters.

12. A spinal syringe and needle combination for holding and dispensing a drug to be injected spinally into a patient, the combination not operatively connectable with a typical syringe and typical needle combination, the typical needle having a syringe connecting opening for connecting the typical needle to the typical syringe, said spinal syringe and needle combination further comprising:
   (a) the spinal needle comprising a needle engagement extension defining an opening of predetermined external diameter;
   (b) the spinal syringe comprising a syringe engagement extension comprising a nozzle defining a conduit of a pre-determined internal diameter, the syringe engagement extension engageable with the needle engagement extension to operatively connect the needle to the syringe to permit the drug in the spinal syringe to be injected through the spinal needle on actuation of the spinal syringe; and
   (c) the external and internal diameters are dimensioned such that:
      (i) a surface of the needle engagement extension defining the opening is in frictional engagement with a surface of the nozzle defining the conduit;
      (ii) the external diameter of the needle engagement extension opening is larger than the internal diameter of a nozzle of the typical syringe; and
      (iii) the internal diameter of the nozzle is less than the external diameter of the syringe connecting opening of the typical needle.

13. The combination of claim 12 wherein the second internal diameter of the nozzle is larger than the external diameter of the syringe such that the inner surface of the nozzle is in frictional engagement with the outer surface of the needle engagement extension.

14. The combination of claim 12 wherein the external diameter of the syringe engagement extension is greater than 3.527 millimeters and the internal diameter of the nozzle is less than 7.73 millimeters.

15. The combination of claim 12 wherein the needle engagement extension has a pre-determined internal diameter which is less than 3.925 millimeters and the nozzle has a pre-determined external diameter greater than 4.315 millimeters.

16. The combination of claim 12 wherein the inner and outer surfaces are conical and the dimensions are compared at the smallest external diameter of the syringe engagement extension and the largest internal diameter of the nozzle.

17. A system for preventing the inadvertent injection of a spinal drug intravenously and an intravenous drug spinally where a patient requires both intravenous injection of the intravenous drug and spinal injection of the spinal drug, comprising in combination:
   (a) a spinal needle;
   (b) a spinal syringe for holding and dispensing the drug to be injected spinally into a patient, the spinal syringe operatively connectable to the spinal needle to permit the drug in the spinal syringe to be injected through the spinal needle on actuation of the spinal syringe;
   (c) an intravenous needle;
   (d) an intravenous syringe for holding and dispensing the drug to be injected intravenously into a patient, the intravenous syringe operatively connectable to the intravenous needle to permit the drug in the intravenous syringe to be injected through the intravenous needle on actuation of the intravenous syringe;
   (e) the intravenous needle cannot be operatively connected with the spinal syringe thereby preventing the inadvertent injection of the drug in the spinal syringe through the intravenous needle; and
   (f) the spinal needle cannot be operatively connected with the intravenous syringe thereby preventing the inadvertent injection of the drug in the intravenous syringe through the spinal needle.

18. The system as described in claim 17 wherein:
   (a) the spinal needle comprises a first Luer lock portion at an end of the spinal needle;
   (b) and the spinal syringe comprises a second Luer lock portion at an end of the spinal syringe which mates with the first Luer lock portion of the spinal needle to operatively connect the spinal needle with the spinal syringe;
   (c) the intravenous needle comprising a first slip fit portion on an end of the intravenous needle; and
   (d) the intravenous syringe comprises a second slip fit portion on an end of the intravenous syringe which mates with the first slip fit portion of the intravenous needle to operatively connect the intravenous needle with the intravenous syringe.

19. The system as described in claim 17, wherein:
   (a) the spinal needle includes a first end for insertion into the patient and a second end opposite the first end, and wherein the second end includes a spinal needle connector;
   (b) the spinal syringe includes a first end, the first end having a spinal syringe connector attached thereto, the spinal syringe connector operatively connectable to the spinal needle connector to permit the drug in the spinal syringe to be injected through the spinal needle on actuation of the spinal syringe;
   (c) the intravenous needle includes a first end for injection into a patient and a second end, and wherein the second end includes an intravenous needle connector; and
   (d) the intravenous syringe includes a first end having an intravenous syringe connector attached thereto, the intravenous syringe connector operatively connectable to the intravenous needle connector to permit the intravenous drug in the intravenous syringe to be injected through the intravenous needle on actuation of the intravenous syringe.

20. The system as described in Clam 19 wherein:
   (a) the spinal needle connector comprises a first Luer lock portion and the spinal syringe connector comprises a second Luer lock portion which mates with the first Luer lock portion; and
   (b) the intravenous needle connector comprises a first slip fit portion and the intravenous syringe connector comprises a second slip fit portion which mates with the first slip fit portion.

21. The system as described in claim 19 wherein:
   (a) the spinal needle connector comprises a first slip fit portion and the spinal syringe connector comprises a second slip fit portion which mates with the first slip fit portion; and
   (b) the intravenous needle connector comprises a first Luer lock portion and the intravenous syringe connector comprises a second Luer lock portion which mates with the first Luer lock portion.

22. The system as described in claim 19 further comprising an elongated spinal needle passage having an opening therethrough connected to the spinal needle connector and an elongated intravenous syringe passage having an opening therethrough connected to the intravenous syringe connector; wherein the internal diameter of the opening in the intravenous syringe passage is less than the external diameter of the spinal needle passage and wherein the internal diameter of the opening through the spinal needle passage is less than the external diameter of the intravenous syringe passage.

23. The system as described in claim 22 wherein the spinal syringe connector comprises a spinal syringe passage extending therefrom and having an opening therethrough with an internal diameter slightly larger than the external diameter of the spinal needle passage to permit friction fit releasable connection between the spinal needle passage and the spinal syringe passage to operatively connect the spinal needle to the spinal syringe.

24. The system as described in claim 23 wherein the intravenous needle connector includes an intravenous needle passage having an inner diameter less than the outer diameter of the spinal syringe connector and an outer diameter greater than the inner diameter of the spinal syringe connector.

25. The system as described in claim 19 wherein the spinal needle further comprises an opening therethrough to direct liquid in the spinal syringe through the spinal needle opening into the patient and wherein the system further comprises a stylus with a first end and a second end and a stylus head connected to the second end of the stylus, the stylus dimensioned in diameter for insertion through the spinal needle opening and dimensioned in length to extend to the first end of the needle when the stylus head contacts the second end of the needle.

26. The system as described in claim 25 wherein the intravenous needle further comprises an opening therethrough to direct liquid in the intravenous syringe through the intravenous needle opening into the patient, the stylus dimensioned in width larger than the intravenous needle opening to prevent insertion of the stylus into the intravenous needle opening.

27. The system as described in claim 19 wherein the spinal syringe further comprises indicia notifying a user to fill the syringe only with a drug intended to be injected spinally.

28. The system as described in claim 27 wherein the intravenous syringe further comprises indicia notifying a user to fill the syringe only with a drug intended to be injected intravenously.

29. The system as described in claim 17 wherein the spinal needle comprises interference means for preventing operative connection with the intravenous syringe while permitting operative connection of the spinal needle with the spinal syringe.

30. The system as described in claim 29 wherein the interference means comprises a contact positioned on the spinal needle to prevent operative connection of the spinal needle with the intravenous syringe and wherein the spinal syringe includes a contact receptacle for receiving the contact and permitting operative connection of the spinal syringe to the spinal needle.

31. The system as described in claim 17, wherein the spinal needle connector is incompatible for operative connection with both a Luer lock system of attaching a needle to a syringe and a slip fit system for attaching a needle to a syringe.

32. In a drug delivery system for ensuring the delivering a spinal drug spinally and an intravenous drug intravenously, the combination comprising:
    (a) a spinal syringe;
    (b) a spinal needle operatively connectable with the spinal syringe;
    (c) an intravenous syringe;
    (d) an intravenous needle operatively connectable with the intravenous syringe;
    (e) the intravenous syringe being incompatible with the spinal needle to prevent the operative connection of the intravenous syringe with the spinal needle thereby preventing the inadvertent injection of an intravenous drug in the intravenous syringe spinally through the spinal needle; and
    (f) the spinal syringe being incompatible with the intravenous needle to prevent the operative connection of the spinal syringe with the intravenous needle thereby preventing the inadvertent injection of a spinal drug in the spinal syringe intravenously through the intravenous needle.

33. A system for preventing the inadvertent injection of a spinal drug intravenously and an intravenous drug spinally where a patient requires both intravenous injection of a drug and spinal injection of another drug and where the system includes a set of spinal and intravenous needle and syringe components provided together for substantially concurrent use, characterised in that:
    (a) the spinal needle includes a spinal needle connector;
    (b) the spinal syringe comprises a spinal syringe reservoir for holding the drug to be injected spinally, the spinal syringe having a spinal syringe connector operatively connectable to the spinal needle connector to permit the drug in the spinal syringe reservoir to be injected through the spinal needle;
    (c) the intravenous needle includes an intravenous needle connector;
    (d) the intravenous syringe comprises an intravenous syringe reservoir for holding the drug to be injected intravenously, the intravenous syringe having an intravenous syringe connector operatively connectable to the intravenous needle connector to permit the intravenous drug in the intravenous syringe reservoir to be injected through the intravenous needle;
    (e) the intravenous needle connector is incompatible for operative connection with the spinal syringe connector; and
    (f) the spinal needle connector is incompatible for operative connection with the intravenous syringe connector.

34. A method of preventing the inadvertent injection of a spinal drug intravenously and an intravenous drug spinally comprising the steps of:
    (a) filling a syringe reservoir of a spinal syringe with a spinal drug;
    (b) filling a syringe reservoir of an intravenous syringe with an intravenous drug;
    (c) inserting a distal end of a spinal needle into the spinal cavity of a patient such that a proximal end of the spinal needle extends from the patient;
    (d) connecting the spinal syringe to the proximal end of the spinal needle, the spinal needle incompatible with and not operatively connectable to the intravenous syringe;
    (e) connecting an intravenous needle to the intravenous syringe, the intravenous needle incompatible with and not operatively connectable to the spinal syringe;
    (f) injecting the spinal drug into the spinal cavity of the patient using the spinal syringe and needle; and
    (g) injecting the intravenous drug intravenously into the patient using the intravenous syringe and needle.

35. A system for preventing the inadvertent injection of a spinal drug intravenously and an intravenous drug spinally where a patient requires both intravenous injection of a drug and spinal injection of another drug, the system comprising:
    (a) a set of spinal and intravenous needle and syringe components provided together for substantially concurrent use;
    (b) the spinal needle of the set being incompatible for operative use with the intravenous syringe; and
    (c) the intravenous needle of the set being incompatible for operative use with the spinal syringe.

* * * * *